United States Patent [19]

Takeya et al.

[11] Patent Number: 5,380,935
[45] Date of Patent: Jan. 10, 1995

[54] PROCESS FOR PREPARING 5-AMINOLEVULINIC ACID

[75] Inventors: Haruhiko Takeya; Toshio Shimizu; Hiroyuki Ueki, all of Satte, Japan

[73] Assignees: Cosmo Research Institute; Cosmo Oil Co., Ltd., both of Tokyo, Japan

[21] Appl. No.: 183,289

[22] Filed: Jan. 19, 1994

[30] Foreign Application Priority Data

Jan. 20, 1993 [JP] Japan .................................. 5-7738
Dec. 3, 1993 [JP] Japan ................................ 5-303791

[51] Int. Cl.$^6$ ............................................ C07C 229/00
[52] U.S. Cl. .............................. 562/567; 204/157.69
[58] Field of Search ........................................ 562/567

[56] References Cited

U.S. PATENT DOCUMENTS 3,846,490 11/1974 Aronova .............................. 562/567
5,284,973 2/1994 Ebata .................................. 562/567

Primary Examiner—Michael L. Shippen
Attorney, Agent, or Firm—Oblon, Spivak, McClelland, Maier & Neustadt

[57] ABSTRACT

A process for preparing 5-aminolevulinic acid or a salt thereof, which comprises reacting furfurylamine, of which the amino group has been protected, with oxygen molecule under irradiation by light in the presence of a sensitizer; hydrogenating the resulting compound in the presence of a metallic catalyst; and hydrolyzing the hydrogenated compound. 5-Aminolevulinic acid, useful as a raw material for various chemicals and as an agricultural chemical, can be prepared at a high yield by a simple procedure from a raw material which is inexpensive and readily available.

7 Claims, No Drawings

PROCESS FOR PREPARING 5-AMINOLEVULINIC ACID

BACKGROUND OF THE INVENTION

1. Field of the Invention

The present invention relates to a process for preparing 5-aminolevulinic acid or a salt thereof which is useful as a raw material for various chemicals and is an agricultural chemical. The process can be applied to the industrial manufacture of 5-aminolevulinic acid with advantage.

2. Description of the Background Art

5-Aminolevulinic acid is an intermediate for biosynthesis of haem, vitamin $B_{12}$, and cytochrome. It is known to be a useful compound as a raw material for various chemicals and also as an agricultural chemical. This compound has been reported to exhibit a selective herbicidal action by Revitz et al. at Illinois University.

The 5-aminolevulinic acid can be prepared either by using photosynthetic microorganisms or by chemical synthetic methods. Included in typical known methods of chemical synthesis of 5-aminolevulinic acid are, (1) a method of converting succinic acid into a monoester and introducing a carbon-nitrogen unit into the monoester, followed by reduction; (2) a method of oxidizing levulinic acid to protect the 2- and 3-positions as a double bond, aminating the 5-position carbon atom of the protected compound, and reducing the amino compound; and (3) a method of oxidizing 2-hydroxypyridine to 2,5-dihydroxypyridine, reducing the 2,5-dihydroxypyridine into 2,5-pyperidinedione, and hydrolyzing the 2,5-pyperidinedione.

Problems encountered in the above-mentioned method (1) are the necessity of protecting one carboxyl group of succinic acid, the requirement of using a deadly toxic cyano compound, such as silver cyanide or copper cyanide, for introducing the carbon-nitrogen unit, and also the need for handling toxic compounds such as zinc and the like during the reduction. In the absence of a method of selectively introducing an amino group to a desired position, the method (2) requires the complicated procedure of protecting and removing the protective groups from the positions which otherwise need not be modified. Notwithstanding the comparatively short processing steps involved, the method (3) has drawbacks in the high cost of the raw material 2-hydroxypyridine, the difficulty involved in the availability of this raw material, and the low overall yield of as low as about 8–10%.

More recently, comparatively reasonable methods for synthesizing 5-aminolevulinic acid have been disclosed. One comprises providing N-protected furfurylamine (furfurylamine of which the amino group has been protected), oxidating this compound by electrode or bromine in the presence of methanol, and reducing the oxidated compound, followed by further oxidation with $KMnO_4$. In another method, tetrahydrofurfurylamine obtained by the reduction of furfurylamine is used as a raw material for oxidation with ruthenium oxide.

One problem with these methods is the use of a large quantity of expensive chemical oxidizing agents, which gives rise to a high production cost. In particular, $KMnO_4$ used in the former method cannot be recovered in the form usable as an oxidizer, and therefore must be discarded. Difficulties are encountered in the waste liquid treatment. In addition, because only an insufficient amount of oxidation is achieved in the first oxidation step, the oxidation must be carried out in two stages.

SUMMARY OF THE INVENTION

In view of this situation, the present inventors have undertaken extensive studies and found that 5-aminolevulinic acid can be industrially manufactured with advantage by using N-protected furfurylamine as a starting material, reacting this compound with oxygen ($O_2$) under irradiation by light, and hydrogenating the resulting compound, followed by hydrolysis. This finding has led to the completion of the present invention.

Accordingly, an object of the present invention is to provide a process for preparing 5-aminolevulinic acid or a salt thereof at a high yield by a simple procedure from a raw material which is inexpensive and readily available.

This object of the present invention can be achieved by a process comprising, reacting furfurylamine, of which the amino group has been protected, with oxygen ($O_2$) under irradiation by light in the presence of a sensitizer, hydrogenating the resulting compound in the presence of a metallic catalyst, and hydrolyzing the hydrogenated compound.

Other and further objects, features and advantages of the present invention will appear more fully from the following description.

DETAILED DESCRIPTION OF THE INVENTION AND PREFERRED EMBODIMENTS

The process of the present invention comprises the following three steps, (1) a step of reacting furfurylamine, of which the amino group has been protected, with oxygen under irradiation by light in the presence of a sensitizer (oxidation step), (2) a step of hydrogenating the oxidized compound in the presence of a metallic catalyst (reduction step), and (3) a step of hydrolyzing the hydrogenated compound (hydrolysis step). These steps are considered to proceed according to the following chemical reaction formulas,

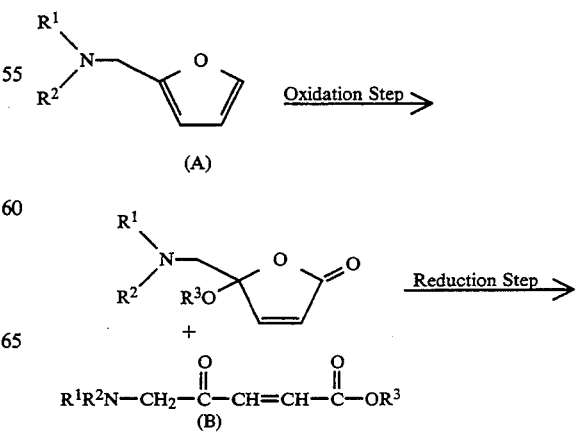

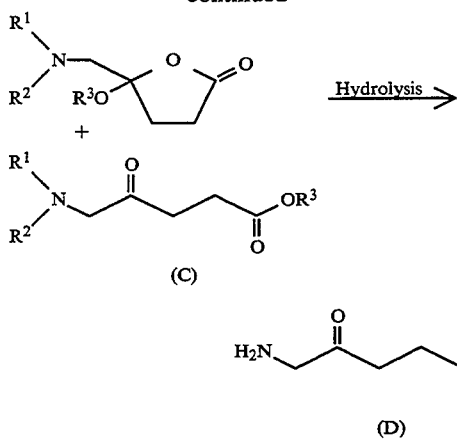

wherein $R^1$ and $R^2$ represent protective groups for amino group and $R^3$ is a hydrogen atom or an alkyl group.

Each step of the process will now be illustrated in detail.

(1) Oxidation Step

The step (1) is a step for oxidizing N-protected furfurylamine (A). The N-protected furfurylamine (A) used as the raw material can be readily synthesized from furfurylamine by a common method (Lecture of New Experimental Chemistry, edited by The Chemical Society of Japan, Vol. 14, Synthesis and Reaction of Organic Compounds V, Maruzen Publishing Co. (1978), page 2558; Organic Syntheses, Vol. 5, John Wiley & Sons (1978), page 944). The protective group may be either a cyclic group, such as phthalimide, or a linear group, with an especially preferred group being acyl group.

The oxidation step can be carried out by dissolving the raw material in a solvent, adding a sensitizer to the solution, and feeding in oxygen gas under irradiation by light.

Pyridine is a preferable solvent used here. A mixture of pyridine (more than 25% by volume) and one or more organic solvents, such as acetone, methyl ethyl ketone, toluene, xylene, benzene, chloroform, dichloromethane, ethyl acetate, methyl acetate, methanol, ethanol, propanol, and isopropanol, can also be used. The amount of solvent used is preferably 3–30 ml per 1 mmol of N-protected furfurylamine.

Commonly used organic coloring agents, such as Rose Bengal, erythrosine, methylene blue, chlorophyll, and hematoprophyrin, as well as polycyclic aromatic compounds, such as coronene and furalene, can be used as the sensitizer. The sensitizer can be used at a concentration of $10^{-2}$–$10^{-5}$ mol/l in the solvent, with the concentration of $10^{-3}$–$10^{-4}$ mol/l being preferred in view of the reaction efficiency and the economy, and for preventing mingling of the sensitizer in the succeeding steps.

Oxygen used as the oxidizer can be oxygen in the air or commercially available oxygen gas. Oxygen atom or ozone is excluded. Oxygen may be used diluted with an inert gas such as nitrogen. The amount of oxygen gas supplied can be suitably determined depending on the concentration of oxygen in the gas, the amount of the solvent, the concentration of the raw material, and the reaction temperature. For instance, when the oxygen gas is fed in under the conditions of a raw material concentration of 100 mmol/l, a Rose Bengal concentration of $10^{-4}$ mmol/l, and at 0° C., a preferable feed rate of the oxygen gas is 5–50 ml/min for 100 ml of the reaction mixture. Because the reaction is effected by the dissolved oxygen, an excessive amount of oxygen is unnecessary, but too small an amount cannot cause the reaction to proceed.

There are no specific limitations as to the source of the light used for irradiation. Any optional sources, such as sunlight, fluorescent lamp, tungsten-halogen lamp, and high-pressure mercury lamp, can be used. Among these, especially preferred are fluorescent lamp, tungsten-halogen lamp, and high-pressure mercury lamp, because of the high energy efficiency of visible lights.

Although a temperature above $-80°$ C. can be employed for the reaction, a range of 0°–25° C. is preferred in view of the efficiency of the reaction and the safety. The reaction is normally completed within 3–15 hours at a temperature in this range.

After the completion of the reaction, the solvent is evaporated to obtain N-protected-5-aminomethyl-5-hydroxy-2,5-dihydrofuran-2-one or its ring-opened isomer, 4-oxo-5-phthalimidopentenic acid, represented by the above formula (B). These are tautomers, changing the properties in the reaction system or depending on the external conditions such as analytical conditions. Although the oxidation product may be purified and isolated by a conventional procedure such as recrystallization, it may be transferred without purification to the next step after decoloration using activated carbon.

(2) Reduction Step (Hydrogenation)

This step is a step for reducing the oxidation product obtained in the preceding oxidation step.

Although any conventionally known method may be applied to this step, hydrogenation using a metallic catalyst is preferred in view of economy of the reaction. The use of a Group VIII metal as the catalyst is preferred. Typical catalysts are palladium, nickel, and Raney nickel, supported on a carrier.

Specifically, this step can be carried out, for example, in methanol in an amount of 5–20 times the raw material using 5% palladium-on-carbon as the catalyst under a hydrogen atmosphere of 1–3 atm and at 0°–50° C. A lower alcohol, such as ethanol or propanol, or a low aliphatic fatty acid, such as acetic acid, can be used as a solvent. Even though alkylation of $R^3$ may take place in the reaction using a lower alcohol as a solvent, the alkylated product may be processed as is without any problem in the preparation of 5-aminolevulinic acid.

After the reaction, the catalyst is removed by filtration and the solvent is evaporated to obtain a solid product, which can be used as is in the next step.

(3) Hydrolysis Step

This step is a step for obtaining 5-aminolevulinic acid by hydrolysis.

The use of an acid is preferable for carrying out the hydrolysis. Because the acid becomes a component of a salt of 5-aminolevulinic acid after the hydrolysis, any optional acids, such as acetic acid, toluenesulfonic acid, hydrochloric acid, and sulfuric acid, can be selected depending on the purposes to which the product is directed.

As a solvent, water or a mixture of water and a water-soluble organic solvent, such as dioxane, tetrahydrofuran, or methanol, can be used.

After the reaction, the solvent is evaporated to obtain the salt of 5-aminolevulinic acid. This salt can be purified by conventionally known methods, such as recrystallization using a water-ethanol mixture or an ethyl acetate-ethanol mixture.

The salt of 5-aminolevulinic acid may be converted to free 5-aminolevulinic acid by neutralization with an equivalent amount of alkali.

The 5-aminolevulinic acid thus prepared can be used as an intermediate for the production of haem, vitamin $B_{12}$, cytochrome, and the like, as an agricultural chemical, or as a raw material for the manufacture of various chemicals.

According to the process of the present invention, 5-aminolevulinic acid can be prepared at a high yield by a simple procedure from a raw material which is inexpensive and readily available. The process thus bears a high value industrially.

Other features of the invention will become apparent in the course of the following description of the exemplary embodiments which are given for illustration of the invention and are not intended to be limiting thereof.

EXAMPLES

Example 1

(1) Oxidation Step 2.27 g (10.0 mmol) of N-furfurylphthalimide was charged into a three-necked glass flask equipped with an oxygen feed tube, a thermometer, and a reflux condenser, and dissolved in 100 ml of anhydrous pyridine. After the addition of 7.0 mg of Rose Bengal, oxygen gas was fed at a rate of 20 ml/min at 10°–20° C. under irradiation by light. A 27 W white fluorescent lamp was used as a light source and the radiation was performed from the outside of the flask. After 7 hours, the irradiation was terminated and the pyridine was evaporated under reduced pressure to obtain 2.47 g of a light brown, semi-crystalline product.

(2) Reduction Step (Hydrogenation)

2.00 g of the semi-crystalline solid obtained in (1) was dissolved in 40 ml of methanol and stirred at 50° C. in a hydrogen atmosphere under atmospheric pressure in the presence of 200 mg of 5% palladium-on-carbon catalyst.

After five hours, the reaction was terminated and the mixture was allowed to cool to room temperature. The catalyst was removed by filtration and methanol was evaporated to obtain 2.11 g of white crystals.

(3) Hydrolysis Step 100 ml of 6N hydrochloric acid was added to 2.11 g of the white crystals obtained in (2), and the mixture was heated under reflux for 5 hours.

After evaporating the hydrochloric acid under reduced pressure, a brown solid product was obtained and dissolved in ethanol. Acetone was added to the solution and the crystals produced were collected by filtration to obtain 0.689 g of 5-aminolevulinic acid hydrochloride. The yield based on N-furfurylphthalimide was 51%.

Spectrum data of the 5-aminolevulinic acid hydrochloride are as follows.

$^1$H-NMR ($\delta$ ppm in $D_2O$, 400 MHz): 2.72 (2H, t, J=6.5 Hz), 2.91 (2H, t, J=6.5 Hz), 4.16 (2H, s).

IR cm$^{-1}$ (Nujor method): 3150, 3100, 3000, 1725, 1495, 1430, 1405, 1395, 1390, 1215, 1195, 1145, 1100, 1080, 1000, 975, 955, 865, 840, 620.

Example 2

2.27 g (10.0 mmol) of N-furfurylphthalimide was charged into a three-necked glass flask equipped with an oxygen feed tube, a thermometer, and a lamp protection tube equipped with a water jacket, and dissolved in 100 ml of anhydrous pyridine. After the addition of 7.0 mg of Rose Bengal, oxygen gas was fed at a rate of 20 ml/min at 10°–15° C. under irradiation by light. A 100 W tungsten-halogen lamp was used as a light source and the radiation was performed from the inside of the flask.

After three hours, the irradiation was terminated and pyridine was evaporated under reduced pressure to obtain a red tar-like product. This tar-like product was dissolved in 100 ml of water, insoluble components were removed by filtration, and the filtrate was concentrated and dried to obtain 2.57 g of the oxidation product in the form of light brown crystals. HPLC analysis of the crystals confirmed the presence of pyridine. The purity of this product, excluding the pyridine, was 85%. NMR analysis confirmed the presence of pyridine and 4-oxo-5-phthalimidopentenic acid. The content of pyridine was measured and found to be 23%, equivalent to moles of the oxidation product. The yield of the oxidation product was 76%.

Spectrum data of the oxidation product thus obtained are as follows.

$^1$H-NMR ($\delta$ ppm in $D_2O$, 400 MHZ): 4.80 (2H, s), 6.84 (1H, d), 7.13 (1H, d), 7.30–8.20 (Ar 7H, m), 8.53–8.61 (Ar 2H, m).

IR cm$^{-1}$ (Nujor method): 1770, 1710, 1630, 1480, 1470, 1420, 1380, 1310, 1195, 1110, 1090, 980, 950, 720, 690, 610, 535.

(2) Reduction Step (Hydrogenation)

2.50 g of the light brown crystals obtained in (1) was reduced in the same manner as in Example 1 to obtain 1.88 g of pale yellow crystals. The crystals were identified to be 5-phthalimido levulinic acid by NMR analysis. The yield was 97%.

Spectrum data of 5-phthalimido levulinic acid thus obtained are as follows.

$^1$H-NMR ($\delta$ ppm in $CDCl_3$, 400 MHZ): 2.61 (2H, t), 2.84 (2H, t), 4.57 (2H, s), 7.57–7.95 (Ar 4H, m).

IR cm$^{-1}$(Nujor method): 1770, 1720, 1710, 1690, 1610, 1460, 1410, 1370, 1310, 1280, 1250, 1230, 1190, 1100, 1080, 1040, 1010, 980, 960, 900, 750, 720, 710, 610, 530, 490, 470.

(3) Hydrolysis Step

The hydrolysis was carried out in the same manner as in Example 1 using 1.80 g of the 5-phthalimido levulinic acid produced in (2) above, to obtain 0.862 g of 5-aminolevulinic acid hydrochloride. The yield based on N-furfurylphthalimide was 75%.

Example 3

The oxidation step was carried out in the same manner as in Example 2, except that a mixture of 60 ml of acetone and 40 ml of pyridine was used as the solvent instead of 100 ml of pyridine in Example 2, to obtain 2.46 g of light brown crystals as the oxidation product, which consisted of pyridine, 5-phthalimidomethyl-5- hydroxy-2,5-dihydrofuran-2-one, and 4-oxo-5-phthalimidopentenic acid. The purity after removal of pyridine was 87% and the yield of the oxidation product was 73%.

This oxidation product was reduced in the same manner as in Example 1 and hydrolyzed to obtain 0.855 g of pale yellow crystals of 5-aminolevulinic acid hydrochloride at an yield of 51% based on N-furfurylphthalimide.

Example 4

The oxidation step was carried out in the same manner as in Example 2, except that a mixture of 50 ml of methanol and 50 ml of pyridine was used as the solvent instead of 100 ml of pyridine in Example 2, to obtain 2.01 g (yield: 59%) of pale yellow crystals as the oxidation product, which consisted of pyridine, 5-phthalimidomethyl-5-hydroxy-2,5-dihydrofuran-2-one, and 4-oxo-5-phthalimidopentenic acid.

This oxidation product was reduced in the same manner as in Example 1 and hydrolyzed to obtain 0.670 g of pale yellow crystals of 5-aminolevulinic acid hydrochloride at an yield of 40% based on N-furfurylphthalimide.

Example 5

The oxidation step was carried out in the same manner as in Example 2, except that a mixture of 50 ml of chloroform and 50 ml of pyridine was used as the solvent instead of 100 ml of pyridine in Example 2, to obtain 2.21 g of light brown crystals as the oxidation product, which consisted of pyridine, 5-phthalimidomethyl-5-hydroxy-2,5-dihydrofuran-2-one, and 4-oxo-5-phthalimidopentenic acid. The purity after removal of pyridine was 86% and the yield of the oxidation product was 65%.

This oxidation product was reduced in the same manner as in Example 1 and hydrolyzed to obtain 0.788 g of pale yellow crystals of 5-aminolevulinic acid hydrochloride at an yield of 47% based on N-furfurylphthalimide.

Example 6

The oxidation step was carried out in the same manner as in Example 3, except that 50 mg of coronene was used as a sensitizer instead of 7.0 mg of Rose Bengal, to obtain 2.26 g of pale yellow crystals as the oxidation product, which consisted of pyridine, 5-phthalimidomethyl-5-hydroxy-2,5-dihydrofuran-2-one, and 4-oxo-5-phthalimidopentenic acid. The yield of the oxidation product was 67%.

This oxidation product was reduced in the same manner as in Example 1 and hydrolyzed to obtain 0.771 g of pale yellow crystals of 5-aminolevulinic acid hydrochloride at an yield of 46% based on N-furfurylphthalimide.

Example 7

The oxidation step was carried out in the same manner as in Example 5, except that 10 mg of furalene ($C_{60}$) was used as the sensitizer instead of 7.0 mg of Rose Bengal, to obtain 2.54 g of light brown crystals as the oxidation product, which consisted of pyridine, 5-phthalimidomethyl-5-hydroxy-2,5-dihydrofuran-2-one, and 4-oxo-5-phthalimidopentenic acid. The yield of the oxidation product was 75%.

This oxidation product was reduced in the same manner as in Example 1 and hydrolyzed to obtain 0.838 g of pale yellow crystals of 5-aminolevulinic acid hydrochloride at an yield of 50% based on N-furfurylphthalimide.

Comparative Example 1

The oxidation step was carried out in the same manner as in Example 2, except that 100 ml of toluene was used as a solvent instead of 100 ml of pyridine in Example 2. The reaction mixture was analyzed by HPLC after three hours and five hours to confirm that no reaction took place.

Comparative Example 2

The oxidation step was carried out in the same manner as in Example 2, except that a mixture of 50 ml of acetone and 50 ml of triethylamine was used as a solvent instead of 100 ml of pyridine in Example 2. The reaction mixture was analyzed by HPLC after three hours and five hours to confirm that no reaction took place.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing 5-aminolevulinic acid or a salt thereof, which comprises,
   reacting furfurylamine, of which the amino group has been protected, with oxygen molecule under irradiation by light in the presence of a sensitizer,
   hydrogenating the resulting compound in the presence of a metallic catalyst, and
   hydrolyzing the hydrogenated compound.

2. The process according to claim 1, wherein the reaction of furfurylamine with oxygen molecule is carried out in pyridine as a solvent.

3. The process according to claim 1, wherein the reaction of furfurylamine with oxygen molecule is carried out in an organic solvent containing 25% by volume or more of pyridine.

4. The process according to claim 3, wherein the organic solvent is a mixture of pyridine and one or more solvents selected from the group consisting of acetone, methyl ethyl ketone, toluene, xylene, benzene, chloroform, dichloromethane, ethyl acetate, methyl acetate, methanol, ethanol, propanol, and isopropanol.

5. The process according to claim 1, wherein the sensitizer is one or more compounds selected from the group consisting of organic coloring agents and polycyclic aromatic compounds.

6. The process according to claim 5, wherein the organic coloring agents are Rose Bengal, erythrosine, methylene blue, chlorophyll, and hematoprophyrin.

7. The process according to claim 5, wherein the polycyclic aromatic compounds are coronene and furalene.

* * * * *